United States Patent [19]

de Munck et al.

[11] 4,356,125

[45] Oct. 26, 1982

[54] PREPARATION OF 2-HYDROXYTETRAHYDROFURAN

[75] Inventors: Nicolaas A. de Munck, Delft; Joseph J. F. Scholten, Sittard, both of Netherlands

[73] Assignee: Stamicarbon, B.V., Geleen, Netherlands

[21] Appl. No.: 256,671

[22] Filed: Apr. 22, 1981

[30] Foreign Application Priority Data

Apr. 23, 1980 [NL] Netherlands .......................... 8002342

[51] Int. Cl.$^3$ ..................... C07C 45/50; C07D 307/20
[52] U.S. Cl. ................................. 549/475; 568/451; 568/454
[58] Field of Search ............... 260/347.8; 568/451, 568/454

[56] References Cited

U.S. PATENT DOCUMENTS

| | | | |
|---|---|---|---|
| 3,937,742 | 2/1976 | Yoo | 568/454 X |
| 4,193,942 | 3/1980 | Gerritsen et al. | 568/454 |
| 4,292,198 | 9/1981 | Gerritsen et al. | 568/454 X |

*Primary Examiner*—Richard Raymond

[57] ABSTRACT

An improved process for the conversion of allyl alcohol with hydrogen and carbon monoxide to form a reaction mixture containing hydroformylation products of 2-hydroxytetrahydrofuran and/or 4-hydroxybutyraldehyde. Allyl alcohol, hydrogen, and carbon monoxide are passed, in a gaseous phase, into contact with a catalyst comprised of a solid porous carrier material containing within its pores a solution of a catalytically active metalloorganic complex dissolved in at least one ligand-forming compound, which solution has a vapor pressure of less than 1.3 mbar under the reaction conditions applied. The improved process is preferably carried out on a continuous basis.

8 Claims, No Drawings

PREPARATION OF 2-HYDROXYTETRAHYDROFURAN

BACKGROUND OF THE INVENTION

The invention relates to a process for the preparation of 4-hydroxybutyraldehyde and/or 2-hydroxytetrahydrofuran formed by cyclization of 4-hydroxybutyraldehyde.

It is known that these compounds can be obtained by reaction of allyl alcohol with carbon monoxide and hydrogen by hydroformylation in the presence of a noble metal complex, in particular a rhodium complex. According to German Patent Application No. 2,538,364, the hydroformylation is performed batchwise as a homogeneous liquid phase catalytic reaction wherein the rhodium complex is present as a solution in an inert solvent. Further steps are thus required to recover the catalyst from the reaction product.

This known method of hydroformylation of allyl alcohol also may result in the formation of by-products such as 2-hydroxymethylacetaldehyde (formed by hydroformylation of the second position of the allyl alcohol), propionaldehyde (formed by isomerization of allyl alcohol), propanol (a hydrogenation product), and polymers. The primary hydroformylation product of this known process is probably 4-hydroxybutyraldehyde, which can be converted by cyclization to 2-hydroxytetrahydrofuran. Both 4-hydroxybutyraldehyde and 2-hydroxytetrahydrofuran can be converted to 1,4-butanediol.

SUMMARY OF THE INVENTION

The object of the present invention is to provide an improved method for the hydroformylation of allyl alcohol, which method can be performed continuously with a high selectivity toward the desired product, without the catalyst recovery problems attendent to the above-mentioned known process.

According to the invention, allyl alcohol is converted with hydrogen and carbon monoxide in the presence of a catalytically active metal complex. The conversion is performed in a gas phase in the presence of a catalyst consisting of a solid porous carrier material, in the pores of which is a solution of a catalytically active metallo-organic complex dissolved in one or more ligand-forming compounds, which solution has a vapor pressure of less than 1.3 mbar under the reaction conditions applied. The process of the invention is ideally suited for carrying out the conversion on a continuous basis.

The hydroformylation with the improved method according to the invention has a number of distinct advantages. The reaction can be performed continuously and the recovery of the reaction product is very simple. The selectivity towards 4-hydroxybutyraldehyde and/or the cyclic derivative thereof is high, and the reaction can be performed such that the isomerization of the allyl alcohol to propionaldehyde is suppressed.

The temperature at which the reaction is performed must be high enough for both the allyl alcohol and the hydroformylation products formed to be present in gaseous form. A temperature of between about 90° C. and 150° C. is in general appropriate. A temperature of between 100° C. and 130° C. is preferably applied. In this temperature range the catalyst activity is high, yet the temperature is not high enough to cause any significant loss of the metallo-organic complex.

The reaction can be carried out in either a fluidized bed or a fixed bed. The reaction can be effectively performed at a pressure of between about 1 and 35 bar. However, a pressure of between 2 and 5 bar appears most preferable.

The molar ratio between the hydrogen, allyl alcohol, and carbon monoxide reactants should be generally within the range of about 2 to 10:1:2 to 20. The hydrogen and carbon monoxide should be present in a molar ratio of between about 1:1 and 1:5.

Unconverted allyl alcohol and the hydroformylation products formed can be isolated from the reaction mixture by condensation. The allyl alcohol can then be recovered by distillation and recycled to the reactor. In the reactor the main product formed is 4-hydroxybutyraldehyde. However, during the condensation this 4-hydroxybutyraldehyde is almost completely converted to 2-hydroxytetrahydrofuran. 1,4-butanediol can be obtained from either compounds by hydrogenation.

The catalyst used in this improved method consists of a solid porous carrier material, having present in the pores thereof a solution of a catalytically active metallo-organic complex dissolved in at least one ligand-forming compound, which solution has a vapor pressure of less than 1.3 mbar under the reaction conditions applied.

As the carrier material, both organic and inorganic solid porous materials may be used. Examples of suitable carrier materials include silica, zeolites, activated carbon and macroreticular polymers. Preferably, a carrier material is used that has a surface that is organophilic, and that furthermore contains no groups that may promote the formation of by-products and/or deactivate the metallo-organic complex. Suitable examples of such preferred carrier materials include macroreticular polymers containing no alkali or alkaline earth metal ions or acid anions; silica rendered hydrophobic by heating; silica-alumina containing no alkali metal ions; and inorganic materials such as silica, the acid or basic groups of which have been converted to inert hydrophobic groups by treatment with a suitable reagent, for instance by silanization.

Organic polymers that may be considered suitable carrier materials include crosslinked polyacrylates and crosslinked polystyrene, particularly the macroporous polystyrene resins crosslinked with divinylbenzene. Since these polymers may contain ionic impurities originating, for example, from the polymerization catalyst, they should preferably be thoroughly washed before being impregnated with the solution of the metal catalyst. An advantage of using these organic polymer resins as porous carrier materials is that they are pronouncedly organophilic. A disadvantage is, however, that they cannot be utilized in a fluidized bed, and that problems may arise with the heat discharged in a fixed bed, and they may soften at temperatures above about 150° C.

It is preferable to use inorganic carrier materials. A very suitable inorganic carrier is silica rendered hydrophobic by heat treatment at a temperature of at least 700° C. (see for this treatment S. Kondo et al, Journal of Colloid and Interface Science, Vol. 55 No. 2 (1976) p. 421). The material must be completely, or at least substantially, free of alkali metal ions, on the one hand to prevent sintering during the heat treatment, and on the other hand to suppress the aldol condensation of aldehydes formed during the hydroformylation. Carriers that by nature contain acid or basic groups on their surface, such as silica, silica-alumina or alumina, can be made into very suitable carriers by treating them with a suitable reagent to convert the reactive surface groups into inert groups. A silane, having at least one substituent on the silicon atom that reacts with the reactive surface groups, can be effectively utilized as an inertizing agent.

The dimensions of the carrier material particles may vary between approximately 0.01 and 5.0 mm. Particles having a size in the range of between about 0.01 and 0.1 mm are preferably used in fluidized bed applications, whereas for fixed bed applications, a particle size of between about 0.2 and 2.0 mm is preferred.

A suitable carrier material will have a pore volume, after optional preliminary treatment, generally in the range of between about 0.01 and 5 cm$^3$ per gram of carrier, with the diameter of the pores being in general about 2 and 2,000 nm. Preferably, a carrier material is used in which at least some of the pores have a diameter of less than 10 nm.

The loading of the porous carrier material with the solution of the metallo-organic comples may generally be in the range of between about 0.05 and 0.95 cubic centimeters of solution per cubic centimeter of pore volume. Preferably, the catalyst loading applied is between 0.2 and 0.8 cubic centimeters of solution per cubic centimeter of pore volume.

As the central metal atom in the catalytically active metallo-organic complex, the transition metals of Groups V, VI, VII, and VIII of Mendeleef's periodic system, such as Re, Fe, Ru, Os, Co, Rh, Ir, Ni, Pd, and Pt, may be considered. Rhodium, cobalt, ruthenium, and iridium have been found to be particularly suitable. These metals may also be applied as a mixture with one another.

As ligands in the aforementioned metallo-organic complex, organic compounds may be considered that have in the molecule one atom of the Group VB or VIB of Mendeleef's periodic system with a free electron pair, such as P, S, B, Te, Sb, and As, as well as ligands such as CO, H, and δ- and π-bonded alkenes. Suitable also are, for example, the halogenides, such as Cl, Br, and H-, tin-, and germanium II halogenides, and radicals such as acetate, propionate, and readily replaceable ligands such as acetylacetonate, hydrogen, carbon monoxide, tetrahydrofuran, and diolefine. Suitable complexes that may be considered are rhodiumhydridocarbonyltris(triphenylphosphine), cobalthydridotetracarbonyl, rhodiumbis(triphenylphosphine)carbonylchloride, rhodiumhydridobiscarbonylbis(triphenylphosphine) and rhodiumcarbonylchloride-bis(triphenylarsine).

According to the invention, compounds with a vapor pressure of less than 1.3 mbar under reaction conditions that are able to function as ligands in a transition metal complex, may be used as the solvent for the metal complex. These ligand-forming compounds (herein also termed "free ligand") used as the solvent, need not be the same as the ligands present in the original transition metal complex. They may optionally be substituted for one or more ligands of the metal complex. It is in fact probable that the catalytically active metal complex will differ under operational conditions from the metal compound originally dissolved. Suitable ligand-forming compounds for use as the solvent include organic compounds of phosphorus, antimony, or arsenic. Particularly suitable are phosphorus compounds possessing a free electron pair, such as compounds with the formula $PR^1R^2R^3$ or $P(OR^1)(OR^2)(OR^3)$, where $R^1$, $R^2$, and $R^3$ represent aliphatic, aromatic, or alkyl aromatic hydrocarbon groups with 1-20 carbon atoms. Examples are triethylphosphine, tributylphosphine, tricyclohexylphosphine, methyldiphenylphosphine, diethylphenylphosphine, triphenylphosphine, tri-p-tolylphosphine, trinaphthylphosphine, ethylene-di(dimethylphosphine), trimethylphosphite, trimethylolpropanephosphite, triphenylphosphite, triphenylarsine, phenyldimethylarsine, and triphenylstibine. The high-boiling triarylphosphines are preferably used.

The concentration of the metallo-organic complex in the free ligand can vary within wide limits. The upper limit is determined by the solubility of the metallo-organic complex in the free ligand under reaction conditions, while the lower limit is determined mainly by economic and commercial considerations. The range within which the concentration can thus vary is, for example, from about $10^{-1}$ to $10^{-5}$ mole/liter, more preferably $10^{-2}$ to $10^{-4}$ mole/liter.

To prepare the catalyst, the carrier may be impregnated with a solution of the catalytically active metal complex or a precursor thereof dissolved in free ligand without other solvents. Just enough ligand-solvent need be used to achieve the desired loading immediately. It is, however, easier to use an auxiliary solvent in the catalyst preparation. When using an auxiliary solvent, the carrier is impregnated with a solution of the catalytically active metal complex or a precursor thereof and a mixture of one or more free ligands with a volatile auxiliary solvent, and subsequently the volatile solvent is removed. By an inert volatile solvent is meant a composition that does not strongly coordinate with the metallo-organic complex, that has a vapor pressure that is at least ten times higher than the vapor pressure of the free ligand, and that forms a homogeneous solution with the free ligand and the metallo-organic complex. Suitable inert volatile solvents include, for example, methanol, ethanol, benzene, toluene, and xylene.

The proportion of free ligand to inert solvent is governed by the catalyst loading desired. For instance, to obtain a catalyst loading of 0.5, 50 percent of the catalyst solution used should consist of volatile solvent. Just enough catalyst solution is impregnated to fill the complete pore volume of the carrier material in the first instance.

If the ligand is present in solid form at room temperature, the mixture consisting of metallo-organic complex, free ligand, and inert volatile solvent, is heated to the temperature at which a homogeneous solution is obtained. The hot, homogeneous catalyst solution is then slowly added to the carrier material, which has been preheated to a temperature at least equal to the temperature of the catalyst solution. Atmospheric oxygen is excluded throughout this mixing, and the mixture is stirred thoroughly. The impregnation may also be performed in a vacuum.

The free-flowing catalyst thus obtained is thereafter freed of volatile solvent. This can be done by drying the catalyst in vacuo, by the passage of inert gas, or in situ in the reactor in which the hydroformylation takes place, at a temperature at which the volatile solvent evaporates. The drying temperature employed is preferably above the melting point of the free ligand so that redistribution of the free ligand and the carrier material is already possible during the drying of the catalyst.

DETAILED DESCRIPTION OF THE INVENTION

The invention will now be elucidated in detail with reference to the following examples of preferred embodiments, without being restricted to the embodiments described therein.

EXAMPLE I

A catalyst was prepared by impregnating 9.23 g silica (commercial product 000-3E, Akzo Chemie Nederland), having a pore volume of 0.85 cm$^3$/g and a particle size between 0.42 and 0.50 mm, with a solution of 0.148 g rhodiumhydridoocarbonyltris (triphenylphosphine) in 4.04 g triphenylphosphine diluted with an equal quantity of benzene. Subsequently, the benzene was evaporated off. The degree of filling of the pores with the solution of the rhodium complex was then 50% of the catalyst thus obtained.

An amount of 4.68 g of the dried catalyst thus obtained was transferred to a reactor. Allyl alcohol was hydroformylated by passing a mixture of allyl alcohol, hydrogen, and carbon monoxide through the reactor in a volume ratio of 1:4.76:4.76, at a pressure of 3 bar and a temperature of 90° C. The total quantity of gas was 66.3 n.ml/minute. The reaction was carried out continuously for 80 hours. In total, 19.8% of the allyl alcohol applied was converted, 18.7% into 2-hydroxytetrahydrofuran, and 1.1% into propionaldehyde. The selectivity of the hydroformylation was therefore 94.4%. Other products were not found. The activity of the catalyst is 3.4 n.ml allyl alcohol converted per g rhodium (as metal) per second.

EXAMPLE II

A catalyst was prepared in the manner described in Example I by impregnating 8.9 g silica S with a solution of 0.133 g rhodiumhydridocarbonyltris (triphenylphosphine) in 3.22 g triphenylphosphine and benzene followed by the evaporation of the benzene. The degree of filling of the pores was 50%. Silica S is an Na-deficient silica (96 ppm Na) that has been heated for 5 hours at 850° C. The surface area is 100 m$^2$/g, the pore volume 0.99 cm$^3$/g and the mean particle diameter $(dV/dR)_{max}$ is 17 nm. The fraction having a particle size of 1.2 to 1.7 nm was used.

Of the catalyst thus obtained, 5.86 g was transferred to a reactor. A mixture of allyl alcohol, hydrogen, and carbon monoxide in a volume ratio of 1:7.69:7.69 was passed for 62 hours through the reactor at 90° C. and a pressure of 3 bar. The total quantity of gas was 85.2 nml/minute. The conversion of allyl alcohol was 30.6%, with 95% selectivity towards 2-hydroxytetrahydrofuran and 5% towards propionaldehyde. The activity was 3.72 ml allyl alcohol converted per g Rh per second.

Subsequently, a mixture of allyl alcohol, hydrogen, and carbon monoxide in a volume ratio of 1:3.81:3.81 was passed at a quantity of 90.5 nml/minute through the reactor for 62 hours at 110° C. and 3 bar. The conversion was 17.9%, the selectivity towards 2-hydroxytetrahydrofuran was 97.8%, and the activity was 5.06 nml allyl alcohol converted per g Rh per second.

EXAMPLE III

A catalyst was prepared in the manner described in Example I by impregnating 8.84 g silica S with a solution of 0.986 g rhodiumhydridocarbonyltris (triphenylphosphine) in 3.31 g tri-p-tolylphosphine. The degree of catalyst loading was 50%.

A mixture of allyl alcohol, hydrogen, and carbon monoxide in a volume ratio of 1:7.73:7.73 was passed through the reactor, in which 3.1 g catalyst had been introduced, at 88° C. and 4 bar at a quantity of 90.5 nml/minute. The conversion was 6.3%, the selectivity towards 2-hydroxytetrahydrofuran was 81%, and the activity was 1.91 ml allyl alcohol converted per g Rh per second. The duration of the test was 95 hours.

With an increase of the temperature to 108° C., other reaction conditions remaining the same, the conversation became 13.2%, the selectivity toward 2-hydroxytetrahydrofuran became 79.5%, and the activity became 3.93 nml allyl alcohol converted per g Rh per second. The duration of this higher temperature test was 65 hours.

Subsequently, 172.8 nml/minute of a gaseous mixture of allyl alcohol, hydrogen, and carbon monoxide in a volume ratio of 1:7.50:7.50 was passed through the reactor at 108° C. and 4 bar. The conversion was 26.7%, the selectivity 89.8%, and the activity was 11.03 nml allyl alcohol converted per g Rh per second. The duration of this latter test was 80 hours.

In all cases in the above Examples, propionaldehyde was the only by-product that could be found in the reaction product. Formation of this by-product is countered by using a sodium-deficient carrier material. In these 60 to 95 hour tests, no loss of phosphine or metallo-organic complex was observed, and the activity and selectivity remained constant.

What is claimed is:

1. An improved process for the conversion of allyl alcohol with hydrogen and carbon monoxide in the presence of a catalytically active metallo-organic complex to form a reaction mixture containing hydroformylation product selected from the group consisting of 2-hydroxytetrahydrofuran and 4-hydroxybutyraldehyde, the improvement comprising bringing said allyl alcohol, hydrogen, and carbon monoxide, in a gaseous phase and at a temperature of between about 90° C. and 150° C., into contact with a catalyst comprised of a solid porous carrier material containing within its pores a solution of a catalytically active metallo-organic complex in at least one ligand-forming compound, said solution having a vapor pressure of less than 1.3 mbar under the reaction conditions applied.

2. The process of claim 1 wherein said allyl alcohol, hydrogen, and carbon monoxide are continuously introduced into a reaction zone containing said catalyst, and said hydroformylation product containing reaction mixture is continuously withdrawn from said reaction zone.

3. The process of claim 1 or 2 wherein the conversion is performed at a temperature of between 100° C. and 130° C.

4. The process of claim 1 or 2 wherein said conversion is performed at a pressure of between 2 and 5 bar.

5. The process of claim 1 or 2 wherein the molar ratio between hydrogen, allyl alcohol, and carbon dioxide brought into contact with said catalyst is about 2 to 10:1:2 to 10.

6. The process of claim 5 wherein the molar ratio between hydrogen and carbon monoxide is between about 1:1 to 1:5.

7. The process of claim 1 or 2 wherein said carrier material has an organophilic surface that is at least substantially free of acid groups, basic groups and alkali metal ions.

8. The process of claim 1 or 2 wherein said ligand-forming compound within which said catalytically active metallo-organic complex is dissolved is a triarylphosphine.

* * * * *